US005612782A

United States Patent [19]
Keränen et al.

[11] Patent Number: 5,612,782
[45] Date of Patent: Mar. 18, 1997

[54] CALIBRATION METHOD AND CALIBRATION UNIT FOR CALIBRATING A SPECTROMETRIC DEVICE BASED UPON TWO CALIBRATION SAMPLES

[75] Inventors: Heimo Keränen; Mika Christophliemk, both of Oulu, Finland

[73] Assignee: Spectra-Physics Visiontech Oy, Oulu, Finland

[21] Appl. No.: 345,427

[22] Filed: Nov. 21, 1994

[30] Foreign Application Priority Data

Nov. 22, 1993 [FI] Finland .................. 935180

[51] Int. Cl.⁶ .............. G01J 1/02; G01N 21/55; G01D 18/00; G12B 13/00
[52] U.S. Cl. ............ 356/243; 356/448; 250/252.1
[58] Field of Search ............ 356/243, 445, 356/448; 250/252.1 A

[56] References Cited

U.S. PATENT DOCUMENTS

| | | | |
|---|---|---|---|
| 3,832,070 | 8/1974 | Cox | 356/243 |
| 4,029,419 | 6/1977 | Schumann, Jr. et al. | 356/448 |
| 4,465,929 | 8/1984 | Edgar | 250/252.1 |
| 4,566,798 | 1/1986 | Haas | 356/448 |
| 4,803,374 | 2/1989 | Monfort et al. | 356/446 |
| 5,252,038 | 11/1994 | Schmidt et al. | 356/448 |

FOREIGN PATENT DOCUMENTS

| | | | |
|---|---|---|---|
| 0098075 | 1/1984 | European Pat. Off. | |
| 0250959 | 1/1988 | European Pat. Off. | 356/448 |
| 5026625 | 2/1993 | Japan | |
| 2122768 | 1/1984 | United Kingdom | 356/243 |

*Primary Examiner*—Georgia Y. Epps
*Assistant Examiner*—Jason D. Eisenberg
*Attorney, Agent, or Firm*—Sughrue, Mion, Zinn, Macpeak & Seas

[57] ABSTRACT

A calibration method especially for calibrating a reflection spectrometric gauge, such as an oil film gauge. In the method, calibration is conducted by measuring the gauge response by means of a calibration unit and a solid, stable permanent sample (37) provided on it as a calibration sample. A change that simulates a certain substance concentration is generated by the stable permanent sample (37) in the reflection spectrum, and the gauge response is calibrated on the basis thereof. In the invention, the gauge response is calibrated by using at least two calibration samples (37, 39) having different absorption responses, said two calibration samples being said permanent sample (37) and a second calibration sample (39). For calibration, roughness compensation is performed, in which the gauge response is corrected on the basis of the measurement of the optical response of the surface to be measured and the known data on roughness dependence.

12 Claims, 3 Drawing Sheets

CALIBRATION METHOD AND CALIBRATION UNIT FOR CALIBRATING A SPECTROMETRIC DEVICE BASED UPON TWO CALIBRATION SAMPLES

BACKGROUND OF THE INVENTION

The invention relates to a calibration method especially for calibrating a reflection spectrometric gauge used for measuring the quantity of a substance, such as oil, found as a thin film-like layer on a metal surface. Calibration is conducted by measuring the gauge response by means of a calibration unit and a solid, stable permanent sample provided on it as a calibration sample; and a change that simulates a certain substance concentration, e.g. oil concentration, is generated by the stable permanent sample in the reflection spectrum and utilized in calibrating the gauge response electronically, by software, or in some other way.

The invention also relates to a calibration unit especially for a reflection spectrometric gauge, comprising a support with one or several sections, a reflecting surface provided on the support, and a solid, translucent permanent sample provided on the reflecting surface.

The present invention relates to calibration of gauges operating on a reflection measurement principle, especially to calibration of IR analyzers, such as oil film gauges. An oil film gauge can be used for measuring the thickness of an oil film on a metal surface, such as a steel plate. With the gauge, the thickness of an oil film is measured by bringing the optical detector of the gauge to the vicinity of the surface to be measured, whereby the optics of the detector measure the reflection spectrum of the object within a certain wavelength range. The operation of an oil film gauge is based on partial absorption of the radiation emitted by the gauge into the surface measured. In gauges based on absorption spectroscopy, e.g. in oil film gauges, measurement is conducted by determining changes in the absorption of the radiation reflected from a substance in relation to the wavelength. The measurement is based on reflection spectrometry, in which IR radiation emitted from the light source of the gauge passes through an oil film found e.g. on a steel plate and measures the frequency of the functional groups, such as $CH_2$ and $CH_3$ groups, of the oil film in the sample by being reflected from the reflecting surface that underlies the oil film, such as the surface of the steel plate under examination, to the detector. On the basis of the reflection spectrum, the thickness of the oil film on the surface to be measured can be determined.

The reliability and accuracy of the measurement depend on the accuracy by which a spectral change caused by a measuring parameter, such as the thickness of an oil film, can be measured. The most significant factors that cause inaccuracy include changes in the intensity and radiation spectrum of the radiation source of the gauge, instability of the optical components used for separating wavelength ranges to be measured, changes in the geometry of the optics, drifting of the radiation detector components, and any changes occurring on the optical path of radiation, such as dirtying of the optics of the gauge.

To compensate for the errors caused by the above sources of error, the response, i.e. sensitivity, of the gauge has to be calibrated. Calibration is necessary to correct both the drifting of the signal levels of the gauge itself and the differences between different gauges. The purpose of the calibration is to make sure that the slope and zero point of the response graph are correct. If linearity is supposed, the response graph is a straight line.

In some known solutions for calibrating oil film gauges, an even oil film of a predetermined thickness is provided on a calibration unit, such as a sheet metal unit, and the response parameters of the gauge are adjusted by software in such a way that the gauge indicates the thickness of a known sample. However, an oil sample is unstable, and slow and difficult to produce.

Previously known are also such solutions according to the above introduction where a solid, stable, artificial permanent sample is provided on a calibration unit. The use of a permanent sample facilitates measurement and enhances reliability. This kind of solution is presented in European Patent 0,098,075. In the solution concerned, however, it is not possible to take into account all the factors that produce errors in calibration, especially not differences in the roughness of the objects to be measured. In the above-mentioned solution, the response line cannot be determined in a quick and simple manner, since there are no separate samples there that could be measured separately.

SUMMARY OF THE INVENTION

The object of the present invention is to provide a new kind of calibration method and calibration unit, by which the problems of the known solutions are avoided.

The above-mentioned object is achieved with the calibration method of the present invention, which is characterized in that the gauge response is calibrated by using at least two calibration samples having different absorption responses, said two calibration samples representing a first permanent calibration sample and a second calibration sample. Compensation is performed to compensate for response changes caused by differences in the roughness of the surfaces measured. During the roughness compensation, the optical response of the surface is measured, and the gauge response is corrected on the basis of the optical response of the surface to be measured and the known data on roughness dependence.

The above object is achieved with the calibration unit of the present invention, which is characterized in that it also comprises a second calibration sample, and that the absorption responses determined on the basis of the first permanent calibration sample and the second permanent calibration sample differ from each other.

Both the calibration samples are permanent samples, but the second calibration sample, or second permanent sample, may be a bare reflecting surface.

The calibration method and calibration unit of the present invention are advantageous in many respects. The invention makes it possible to take into account, in calibration, the differences in the roughness of the different surfaces to be measured. In the present invention, the roughness compensation of the surfaces to be measured can thus be calibrated in a manner that is easy to perform and improves measuring accuracy. The calibration method as such is new, reliable and easy to perform. The use of two calibration surfaces that produce a different absorption response facilitates determination of the gauge response, and one of these surfaces can also be utilized when roughness compensation is calibrated, particularly when it is normalized.

BRIEF DESCRIPTION OF THE DRAWINGS

In the following the invention will be described in greater detail with reference to the attached drawings, in which.

DETAILED DESCRIPTION OF THE INVENTION

Figure 3:
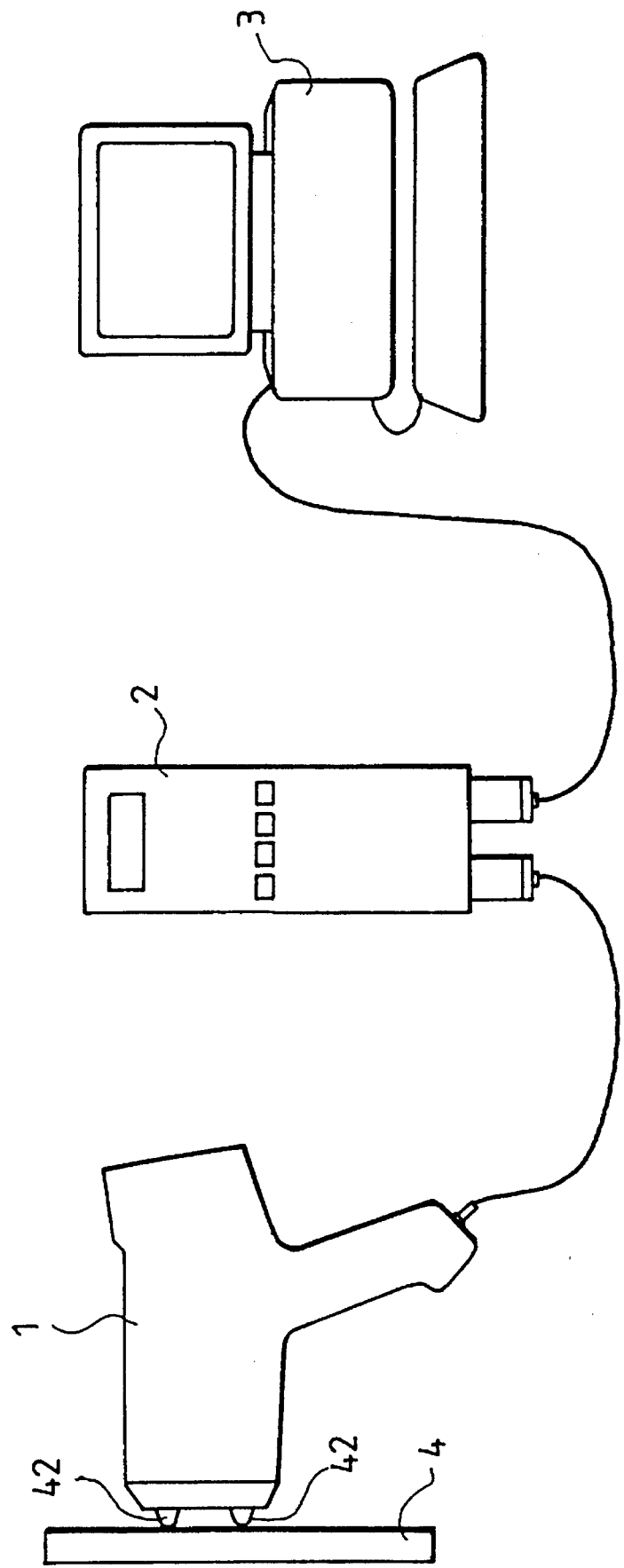
FIG. 3 shows measuring equipment according to the present invention.

The measuring equipment as shown in FIG. 3 comprises a gauge 1, a unit 2 collecting and feeding data, and equipment 3 for presenting and modifying the data, implemented e.g. as a PC. Reference number 4 stands for a slushing-oil-coated steel plate, the thickness of this slushing oil layer being the object of the measurement process.

Figure 1:
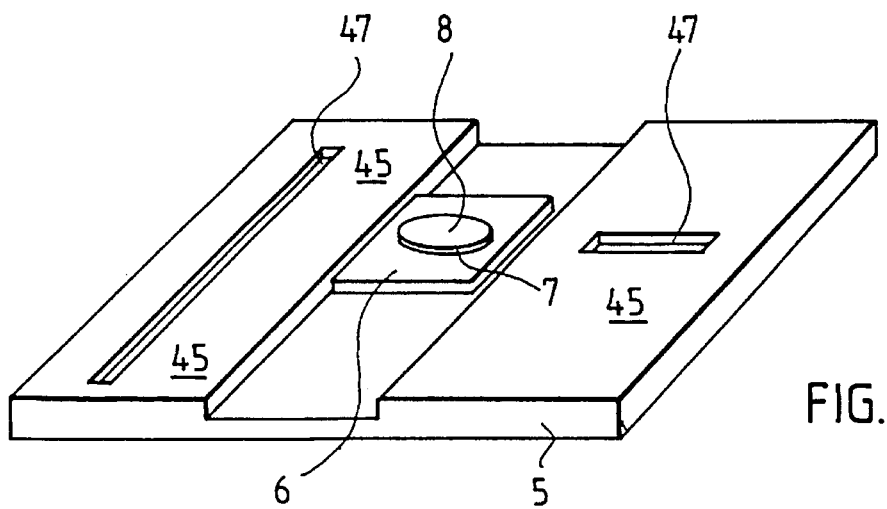
FIG. 1 shows a calibration unit having one reflecting surface.

For calibrating the gauge 1, a calibration unit as shown in FIG. 1 is needed. The calibration unit comprises a support 5, a reflecting surface 6 provided on the support 5, and a translucent permanent sample film 7 provided on the reflecting surface 6. The support 5 may be a 5 mm-thick steel plate. The permanent sample film 7 is a solid, translucent, artificial permanent sample, which between the reflecting surface 6 and a protective coating 8 of the calibration unit, such as sapphire glass, generates holding power by which it fastens without clearances both to the protective coating 8 and to the reflecting surface 6. In calibration, the gauge is supported on a calibration unit in such a way that the IR radiation emitted by the gauge passes through the sapphire glass 8 and the permanent sample film 7, is reflected from the reflecting surface 6 again through the permanent sample film 7 and further to the detector of the gauge 1. The translucence of the permanent sample film 7 means that in calibration, the light emitted by the gauge, such as IR (infrared) light, passes through the permanent sample film. In an advantageous embodiment, the permanent sample film 7 consists of a polymer film polymerized from a monomer. The permanent sample film 7 simulates the actual film to be measured, and so it is selected in such a way that the spectral changes caused by the sample film 7 essentially correspond to the spectral changes caused by the actual film, such as an oil film, to be measured.

Figure 2:
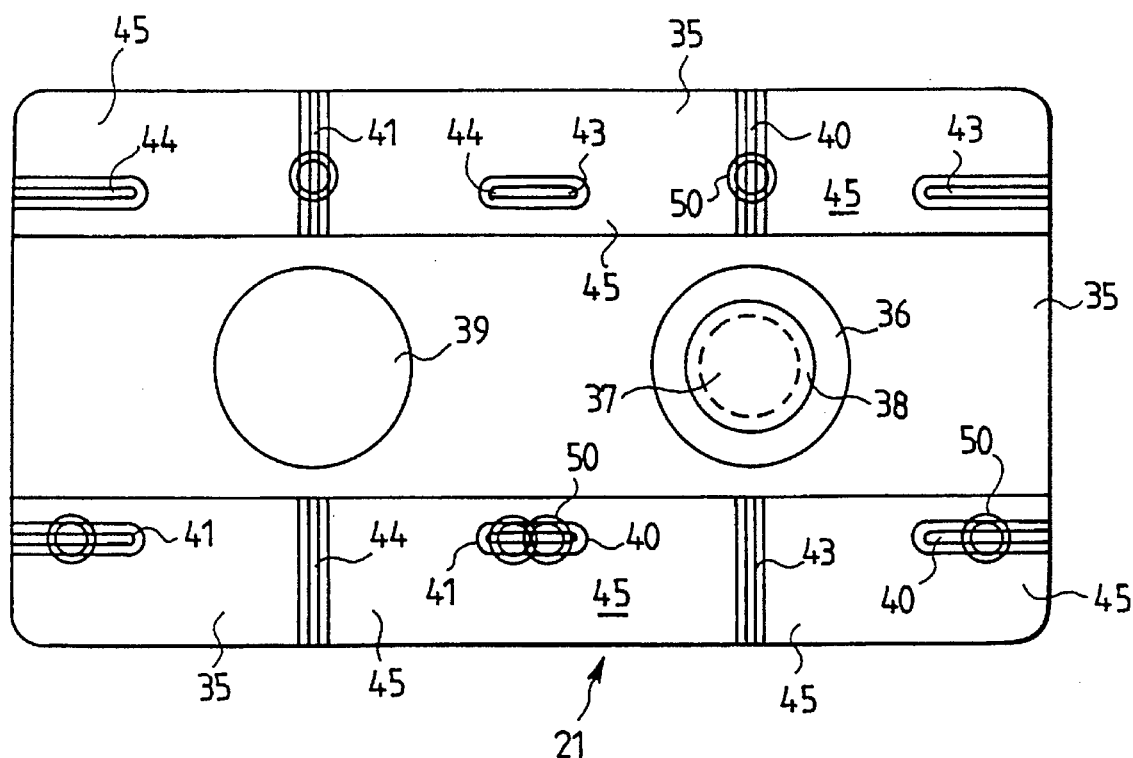
FIG. 2 shows a calibration unit according to an embodiment of the present invention having two reflecting surfaces.

With reference to FIG. 2, we now describe one advantageous embodiment of the invention. A calibration unit 21 shown in FIG. 2 comprises a support 35, a reflecting surface 36 provided on the support 35, and a translucent permanent sample film 37 provided on the reflecting surface 36; the permanent sample film being protected by a protective coating 38, such as sapphire glass. In addition, the calibration unit of FIG. 2 comprises a second reflecting surface 39. The bare reflecting surface 39, advantageously without any permanent sample film, is provided on the same support as the reflecting surface 36 coated with the permanent sample film 37. For the calibration method, two reflecting surfaces with different concentrations are needed, i.e. two surfaces with different coatings; they may be in one and the same unit, as in FIG. 2, or alternatively in different units. At least one of the reflecting surfaces, here e.g. reflecting surface 36, should be coated with a thin artificial permanent sample film 37. The other reflecting surface may be a bare, advantageously smooth, reflecting surface, such as surface 39. This other reflecting surface 39 can also be coated with an artificial permanent sample, although in fact surface 39 as such is a permanent sample (second permanent sample). Permanent sample 39 is the first permanent sample. FIG. 2 also shows position means 40, 41, 43, 44 and 47; gauge contact means 42; and insulation 45. Reference number 50 indicates an imaginary position of the contact means 42 of the gauge.

Figure 4:
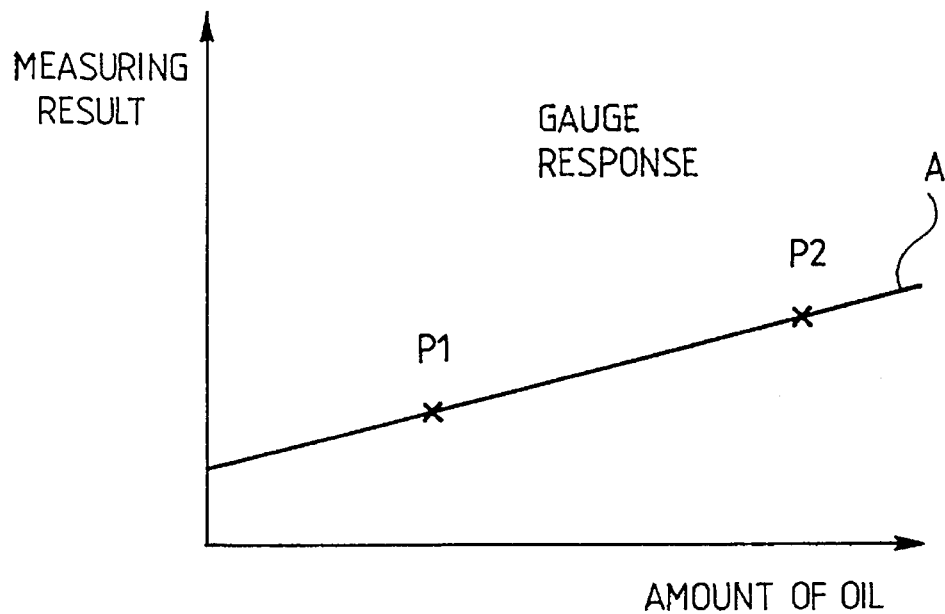
FIG. 4 shows a gauge response line.

In calibration, the gauge measures both surface 36 and surface 39. On account of two surfaces with different concentrations, e.g. reflecting surface 36 with a permanent sample coating 37 and bare reflecting surface 39, it is possible to define two points P1 and P2 in response line A as shown in FIG. 4, and thereby gauge response line A and the slope of response line A, supposing linearity. In FIG. 4 the vertical axis stands for the measuring result obtained with the gauge, and the horizontal axis stands for the measured amount of coating, such as oil. The horizontal axis can also be seen as indicating the oil amount simulated by calibration units. In the method, on a solid, stable, translucent permanent sample film, such as film 37, a change that simulates various substance concentrations, such as an oil concentration, is generated in the reflection spectrum measured by the gauge and utilized in calibrating the gauge response electronically, by software, or in some other way. In calibration, gauge-specific calibration parameters are determined and stored, and used for correcting the gauge response in measurement. The calibration parameters are determined by comparing the responses measured on artificial permanent sample films, such as film 37 or 7, and the required response values stored in the memory of the gauge. These required response values have in fact been defined e.g. by the gauge manufacturer as he has calibrated the gauge, using real samples which have known substance concentrations and are of the same substance, e.g. oil, that is to be measured by the gauge in actual measurement processes. The manufacturer also measures the reflection characteristics of the unit that has been used as an underlayer for the oil sample, and thereby the roughness characteristics of the underlayer, preferably without an oil sample. This first calibration conducted by the gauge manufacturer with oil samples in a laboratory can then be stored as a response parameter corresponding to the calibration unit. This kind of calibration makes it possible to return real and absolutely faultless calibration data to the gauge or to transfer it to another gauge by the calibration unit and the memory of the gauge, or by means of data supplied or transferred to the gauge. The calibration unit also makes it possible to quickly check the gauge response before the actual measurement.

When actual measurement is conducted, the gauge determines the gauge response of the oil concentration of a surface (the right-hand side of the equation) in the following manner:

measuring result=f(gauge)·g(roughness)·h(object measured)·AB(absorption), wherein f(gauge)=correction factor varying with the gauge, calibrated using at least two permanent samples 37, 39, 7 having different absorption responses;

g(roughness)=correction factor caused by the roughness of the surface, determined by measuring the scattering and reflection characteristics of the surface to be measured and by comparing them with the corresponding characteristics of surface 39 (or surfaces) of the calibration unit;

h(object measured)=calibration factor varying with the object measured, dependent e.g. on the type of oil or surface. Function h describes different sets of curves in the graph of function g(roughness) shown in FIG. 5. The user selects suitable preliminary calibration (i.e. function h) e.g. according to the type of oil or surface that is to be measured;

AB(absorption)=absorption function measured at the point of measurement, proportional to substance concentration.

In an advantageous embodiment, the following steps are taken. The gauge response is calibrated in the method by using at least two calibration samples (37, 39, 7) having different absorption responses, i.e. permanent sample 37 (first permanent sample) provided on the reflecting surface 36, and a second calibration sample 39, which advantageously is a bare reflecting surface 39 (second permanent sample). Roughness compensation is conducted to compensate for the response changes caused by differences in roughness on the actual surfaces measured. In roughness compensation, the optical response of the surface is measured. On the basis of this measurement of the optical response on the surface to be measured and the known data on roughness dependence, the gauge response is corrected. To normalize the measurements, an optical response of at least one calibration sample 39 is also always measured. This calibration sample is advantageously the above-mentioned second calibration sample 39 or reflecting surface 39. Surface 39 thus operates as a reference surface. The optical responses measured on the surface to be measured and on the calibration surface 39 are determined on the basis of reflection or scattering.

In roughness compensation of calibration, the optical response of the surface to be measured is measured advantageously simultaneously as the surface itself, when the thickness of the film on the surface to be measured is determined.

In the method according to the present invention, the roughness compensation characteristics of the gauge can thus be calibrated using reflection measurement by defining the optical response that describes the roughness of the surface to be measured, and by modifying gauge response A (FIG. 4) by the response change obtained on the basis of the known data on response-roughness dependence (FIG. 5) stored in the gauge.

In the above manner, the gauge response can be adapted to the roughness of the surface currently measured. This embodiment is based on the observation that the roughness of the surface to be measured affects the result obtained in measuring the thickness of an oil film, in such a way that when the surface is rough, the gauge reading showing the thickness of the oil film is too small, because oil is 'hiding' in the rough surface.

Figure 5:
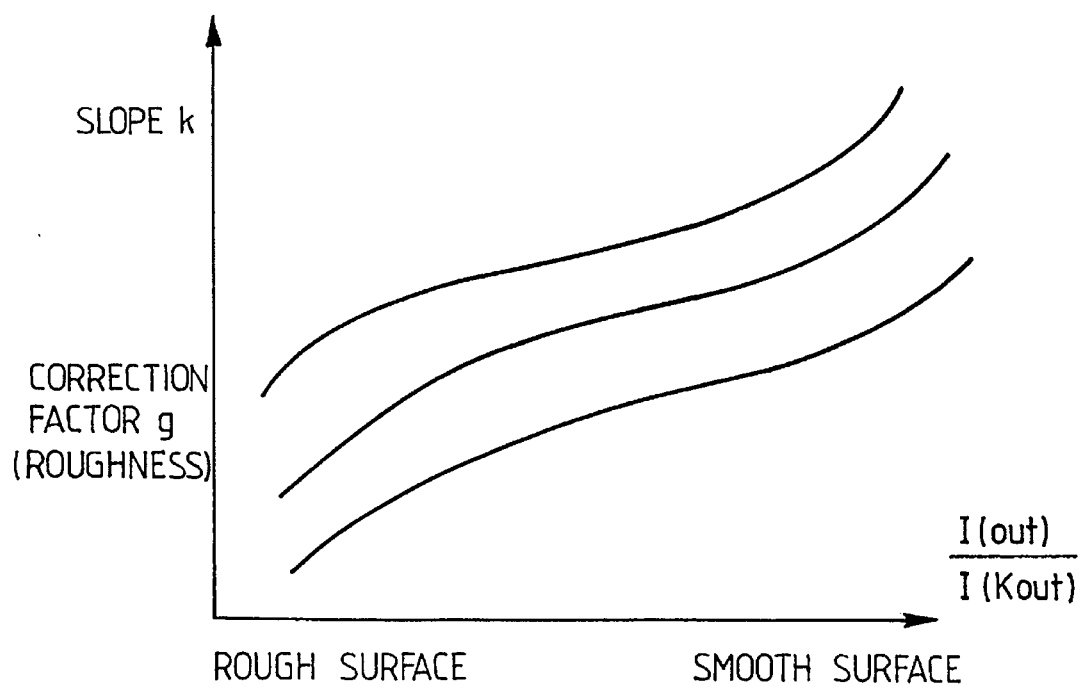
FIG. 5 illustrates the dependence between the slope of the gauge response line and the roughness/ reflection of the surface to be measured.

The rougher the surface, the smaller the slope of the gauge response graph or response line, which describes sensitivity. In extensive measurement processes, it has been possible to show that the slope k of the response line is dependent on the roughness of the surface to be measured. The dependence may be at least partly linear, as shown in FIG. 5. In FIG. 5, the vertical axis stands for the slope k of the response graph, and the horizontal axis stands for the reflection I(out) of the—advantageously cleaned—surface to be measured in relation to the reflection I(K out) of the clean reflecting surface 39 of the calibration unit. The vertical axis can also be seen as describing the inverse value of the above-mentioned correction factor 1/g(roughness). The reflection I(out) value and the value of the above-mentioned reflection relation increase as the surface becomes smoother. This dependence, i.e. the content of FIG. 5, is stored in the memory of the gauge in table form; on account of this dependence data, any changes in the roughness of the surface to be measured can be taken into account so that the change does not produce an error in the calibration or measurement processes. When the user of the gauge in a steel factory starts to measure a steel plate, for example, which has a roughness different from the roughness of the preceding steel plate, the surface to be measured is first cleaned, if necessary, and then measured using a gauge. The result (optical response) obtained represents the reflectivity of the actual surface to be measured, which is dependent on the roughness of the surface. The gauge compares this result obtained by measuring an actual surface to the result (optical response) obtained by measuring a clean calibration surface, such as a clean reflecting surface 39, so as to normalize the measurement. Normalization is important since it prevents errors that could result from impurities in the optics and drifting of the gauge, for any impurities in the optics make the surface look rougher. The curves of FIG. 5 result from different oil or surface types.

In the advantageous embodiment of the invention, if the parameter or optical response describing the reflectivity and thereby roughness of an actual—advantageously cleaned—surface to be measured differs, with actual oil samples, from the reflectivity and thereby roughness (optical response) of the underlayer used by the gauge manufacturer in test calibration, then the gauge modifies the slope of the gauge response line in the above manner in accordance with the dependence table (FIG. 5) programmed in the memory of the gauge in advance, so that a relative change of response corresponds to the relative change that a relative change of roughness has been observed to cause in the extensive tests made.

Although the invention is described above with reference to the examples of the attached drawings, it is to be understood that the invention is not limited thereto but that it can be modified in many ways within the scope of the inventive idea that appears from the attached claims.

What is claimed is:

1. A calibration method for calibrating a reflection spectrometric gauge used for measuring a quantity of a substance forming a thin film-like layer on a surface, said reflection spectrometric gauge comprising a memory for storing gauge response parameters respectively corresponding to known substances and reflection data respectively corresponding to optical responses of known surfaces, and an optical detector, said calibration being conducted with a calibration unit comprising a first sample, and a second sample, said first and second samples having different absorption responses to light, said calibration method comprising the steps of:

irradiating light onto said first sample and said second sample;

detecting reflected light from said first sample and said second sample with said optical detector;

determining an optical response and reflection characteristic data of said first sample and said second sample from said reflected light;

determining gauge response values of said reflection spectrometric gauge based upon said optical response of said first sample and said second sample;

comparing a gauge response value for said first sample with a gauge response parameter, stored in said memory, which corresponds to said substance to be measured;

determining a calibration parameter from said comparison;

determining a surface roughness value of said second sample based upon said reflection characteristic data;

comparing said surface roughness value with reflection data, stored in said memory, of said surface on which said thin film-like layer is formed; and determining a roughness calibration parameter from said comparison.

2. The method according to claim 1, wherein said step of determining said optical response and said reflection data is always performed for at least one of said first sample and said second sample for roughness compensation.

3. The method according to claim 2, said step of determining said optical response includes determining said optical response of said second sample which comprises a reflection surface.

4. The calibration method according to claim 3, wherein optical responses measured from the surface to be measured and the calibration sample (39) are determined on the basis of one of reflection and scattering.

5. The calibration method according to claim 2, wherein said step of determining said optical response comprises the step of determining said optical response based upon one of reflection or scattering.

6. The calibration method according to claim 1, wherein an optical response of said surface on which said substance to be measured is formed is measured simultaneously with said quantity of said substance to be measured.

7. The calibration method according to claim 1, wherein an optical response of said surface on which said substance to be measured is formed is measured from a cleaned surface.

8. The calibration method according to claim 1, further comprising the step of:

modifying a measurement result of said spectrometric gauge in accordance with said roughness calibration parameter when an optical response measured from said surface on which said substance to be measured is formed differs, with said substance formed thereon, from said reflection characteristic data, corresponding to said substance, stored in said memory.

9. The calibration method according to claim 1, further comprising the step of:

determining two points (P1, P2) of a gauge response function using said first and second samples having different absorption responses.

10. A calibration unit for calibrating a reflection spectrometric gauge, comprising:

a support (35), a reflecting surface (36) provided on said support, a first calibration sample (37) provided on said reflecting surface, and a second calibration sample (39), said second calibration sample having an absorption response which is different from an absorption response of said first calibration sample.

11. The calibration unit according to claim 10, wherein said first calibration sample (37) and said second calibration sample (39) are both provided on said support (35).

12. The calibration unit according to claim 10, wherein said second calibration sample (39) is a bare reflecting surface (39).

* * * * *